United States Patent
Stasi

(10) Patent No.: US 11,219,926 B2
(45) Date of Patent: Jan. 11, 2022

(54) MODULABLE SYSTEM FOR IDENTIFYING AND CERTIFYING GARMENTS

(71) Applicant: ADAPTA SPA, Pomezia (IT)

(72) Inventor: Gemma Stasi, Pomezia (IT)

(73) Assignee: ADAPTA SPA, Pomezia (IT)

( * ) Notice: Subject to any disclaimer, the term of this patent is extended or adjusted under 35 U.S.C. 154(b) by 192 days.

(21) Appl. No.: 16/488,404

(22) PCT Filed: Jan. 18, 2018

(86) PCT No.: PCT/IB2018/050301
§ 371 (c)(1),
(2) Date: Aug. 23, 2019

(87) PCT Pub. No.: WO2018/154396
PCT Pub. Date: Aug. 30, 2018

(65) Prior Publication Data
US 2021/0138510 A1      May 13, 2021

Related U.S. Application Data

(63) Continuation-in-part of application No. PCT/IB2018/050301, filed on Jan. 18, 2018.

(30) Foreign Application Priority Data

Feb. 23, 2017   (IT) .......................... 102017000020724

(51) Int. Cl.
*B07C 5/342*   (2006.01)
*B07C 5/36*    (2006.01)
(Continued)

(52) U.S. Cl.
CPC ............ *B07C 5/3422* (2013.01); *B07C 5/362* (2013.01); *G01J 1/4204* (2013.01); *G01K 1/026* (2013.01);
(Continued)

(58) Field of Classification Search
CPC ....... B07C 5/362; G01J 1/4204; G01K 1/026; G01K 3/005; G01K 7/10366; G01K 7/1413
See application file for complete search history.

(56) References Cited

U.S. PATENT DOCUMENTS

2011/0166694 A1 *  7/2011  Griffits .................... G07F 11/72
                                                          700/215

FOREIGN PATENT DOCUMENTS

EP           1004879           5/2000
EP           1004879 A1 *      5/2000    ........... G01N 33/367
(Continued)

OTHER PUBLICATIONS

International Search Report—PCT/IB2018/050301—dated Mar. 22, 2018.

*Primary Examiner* — Terrell H Matthews
(74) *Attorney, Agent, or Firm* — Nixon & Vanderhye

(57) ABSTRACT

Modulable system for identifying and certifying garments, suitable to analyze a garment or an accessory inside a tunnel in which a common movement mechanism transports the garments. The tunnel has image capturing devices, light source and a common automatic gripping mechanism. Each garment has an identification device recognized by an identification sensor in the tunnel. The analysis is performed by software and includes: identification, by associating the garment with a wearer; entry, in which the garment is introduced inside the tunnel; acquisition of the images, in which image capturing devices take at least one pair of photographs; analysis, in which the software analyzes the images; assessment, in which the common dedicated software processes the data and indicates whether the garment meets the pre-set parameters; saving in a memory; sorting the approved garments from those that have been rejected.

(Continued)

The assessment parameters are changeable through a special adjustment device.

20 Claims, 2 Drawing Sheets

(51) Int. Cl.
  *G01J 1/42*  (2006.01)
  *G01K 1/02*  (2021.01)
  *G01K 3/00*  (2006.01)
  *G01N 33/36*  (2006.01)
  *G06K 7/10*  (2006.01)
  *G06K 7/14*  (2006.01)
  *G06T 7/00*  (2017.01)
  *H04N 5/247*  (2006.01)

(52) U.S. Cl.
  CPC ........... *G01K 3/005* (2013.01); *G01N 33/367* (2013.01); *G06K 7/10366* (2013.01); *G06K 7/1413* (2013.01); *G06T 7/0004* (2013.01); *G06T 2207/30124* (2013.01); *H04N 5/247* (2013.01)

(56) References Cited

FOREIGN PATENT DOCUMENTS

| EP | 1122538 | | 8/2001 | |
|---|---|---|---|---|
| EP | 1122538 | A2 * | 8/2001 | ........... G01N 33/367 |
| EP | 2037242 | | 3/2009 | |
| EP | 2037242 | A1 * | 3/2009 | ............ G01J 3/0286 |

* cited by examiner

MODULABLE SYSTEM FOR IDENTIFYING AND CERTIFYING GARMENTS

FIELD OF THE ART

The present invention operates in the field of industrial processes of washing and re-certification of garments, such as high visibility garments for operators who perform high-risk jobs on roads and highways. In particular, the present invention regards a new and innovative method for identifying the garment and for certifying the same through a completely automatic system that allows a quick adaptation to the current laws or specific requests of the client.

PRIOR ART

Safety laws are continuously evolving. In particular, in order to protect the safety of some worker categories, predetermined clothing is obligatory. Often, in fact, it is possible to see firemen, mailmen, employees of the highway management company, road police agents, etc. who wear fluorescent garments with reflector bands. In this manner, even in foggy or rainy conditions, or in any case in poor visibility conditions, wearers present on the road will always be identifiable by drivers who drive in proximity thereto.

It is obvious that each high visibility garment must have parameters predetermined by local or company law in order to be worn by this category of workers.

After each wash, therefore, it is necessary that the garment be newly certified, i.e. the subject who performs the industrial washing must verify that the fabric still has the minimal characteristics in order to have the aforesaid parameters of colorimetry and reflectance.

The 1999 patent EP 1 004 879 has framed the problem and proposed some effective solutions. The object of this patent is a system for acquiring the image of the garment after washing and its comparison with an approved specimen. A dedicated software, at this point, compares each pixel of the two images (that of the specimen and that of the garment under examination) and, in the end, gives feedback on whether the garments comply with the legal parameters.

Such procedure, even if much improved with respect to the preceding re-certification practices, has critical issues that the present patent intends to remedy.

First of all, the patented system obliges the constant presence of an operator at the site of the image acquisition, since an automated system is not provided for sorting the garments deemed suitable from those which do not comply with the parameters. From the colorimetric and spectrophotometric analysis, the system is able to calculate the total surface corresponding to specific parameter characteristics, and in the case of the law 20471, certify the conformity thereof.

Secondly, there is absolutely no system that allows the identification of the garment in its entirety. In many cases, in fact, the wearer must wear both a vest or jacket and pants. The possibility to associate the two garments, during acquisition and processing of the image, would allow being able to control that the entire outfit is in accordance with parameters required by possible modifications to the law and that the sum of the acceptable areas of both garments comply with possible new law requirements. In the case of developments of current law—and without the possibility to sum the garments—with the systems known at the state of the art, many garments could be uselessly discarded.

The analysis of the single garment, without the possibility of identifying it and associating it with other garments simultaneously worn by the wearer, still allows controlling the compliance of small-size garments (S-XS-XXS) with legal parameters, the limited surface of such garments making them more easily positionable at the lower parameter limits. The analysis of the complete outfit of the wearer—currently not existing—would lead to a higher lifetime of the garments, preventing the useless discarding and/or destruction thereof.

Finally, among the critical issues of the systems currently in use, there is no possibility to adjust the parameters according to which a garment is approved or rejected. National and company laws are continuously evolving and they pursue increasingly high safety standards. With the current systems, a change of the law would require resetting and re-installing the software on which the operation of the entire control and/or recertification plant is based. The object of the present patent is therefore that of overcoming these and other critical issues existing in the systems currently used for controlling and/or recertifying garments or accessories.

DESCRIPTION OF THE INVENTION

According to the present invention, a system is attained for analyzing several particular types of garments, in particular high visibility garments, effectively resolving the abovementioned problems.

In addition, the present invention is effectively applied to any type of garment that requires a colorimetric analysis and a calculation of the total surface.

Among the main advantages of the present invention, it should be underlined that the current modes of measuring colorimetric and reflecting characteristics are surpassed; up to now, these have been carried out with instruments such as retroreflectometers and spectrophotometers, through thousands of single measurements for the calculation of the compliant surface.

Advantageously, the present invention makes use of a dedicated software which is adapted to analyze the morphological, metrical and colorimetric state of a garment or an accessory. More in detail, said software, unlike those known up to now, is suitable to overall assess the colorimetric aspects of the garment being analyzed. As global assessment, moreover, it is intended its analysis associated with the size of the garment and with other garments that are worn by the same user. In the case of a work uniform including jacket and pants, it is in fact possible that the single garments are not suitable according to the parameters to be respected—if they are taken separately—while an analysis associated with the other garment could lead to a positive test result.

Said analysis is carried out inside a tunnel, provided with a power supply source and with at least one pair of image capturing devices.

Advantageously, the light source can be constituted by a lamp or a plurality of lamps of any type, such as halogen lamps, LED lamps, UV or IR illuminators, laser lights or the like.

Also the image capturing devices, advantageously, are constituted by cameras or video cameras available on the market, such as CCD video cameras, CMOS video cameras, IR or UV sensors, laser sensors or the like. Said image capturing devices, more specifically, are at least one pair including a front device and a rear device adapted to respectively take a photograph of the front part and a photograph of the rear part of the garment to be analyzed and to send said photographs to the software for the processing thereof.

For the purpose of ensuring that the analysis reaches maximum reliability levels, advantageously, a common automatic gripping mechanism is arranged inside said tunnel. At the time of entry of the garment in the tunnel, said mechanism grips several pre-established strips of the garment to be analyzed and places the latter in a spread configuration. In this manner, substantially the entire surface of the garment to be analyzed is hit by the light of the light source and is visible by said image capturing devices. Of course, at the end of the image capture, said automatic gripping device is adapted to release the gripped strips, returning the garment to the initial configuration.

Advantageously, said tunnel is constituted by a fixed or removable structure in which each garment or the plurality of garments worn by the same wearer remain for a period of time necessary for capturing the images. In some cases, said tunnel can be made in a manner so as to constitute an actual darkroom, in which the light of the outside environment does not at all filter into said tunnel.

In the latter case, advantageously, in order to preserve the functionality of all the components thereof, at least one temperature sensor, preferably a plurality of temperature sensors is placed at the interior of said tunnel. These communicate the interior temperature of the tunnel to the software which, upon exceeding a predetermined threshold value, automatically and reversibly activates a forced ventilation system within the tunnel.

In a preferred embodiment, said tunnel is at its interior also provided with an exposure meter and/or a luxmeter, adapted to monitor the interior brightness in said tunnel in order to control the suitability of the internal light source. Said exposure meter and/or said luxmeter are advantageously also adapted to ensure the absence of light interferences from one image capture step to the next.

The garments to be analyzed, within the system that is the object of the present invention, are moved by a common mechanical movement system advantageously constituted by an entry track, which introduce the garments to the interior of the tunnel, a track inside said tunnel, which the garments remain for the time necessary for capturing the images, and by a pair of exit tracks. In this manner, advantageously, the garments which have been approved in assessment step are sorted from those which have been rejected in assessment step by means of two different channels.

Advantageously, each garment is provided with an identification device, preferably constituted by common barcode readers or RFID readers. Outside or inside the tunnel, a corresponding identification sensor is advantageously placed that is adapted to recognize the garment or the plurality of garments corresponding to the same wearer for a global assessment.

The assessment of the garments takes place according to the following steps:
   A) identification step, in which the garment or the garments corresponding to the same wearer are transported in proximity to the identification sensor by the movement mechanism and are recognized;
   B) entry step, in which said garment to be analyzed, or said plurality of garments corresponding to the same wearer, pass to the track inside the tunnel;
   C) image acquisition step, in which said image capturing devices take at least one pair of photographs for each garment and transmit said images to the dedicated software for processing; during image capture, as explained above, the garment or the associated garments to be analyzed are arranged in a spread configuration by a common automatic gripping mechanism arranged inside said tunnel;
   D) analysis step, in which the dedicated software analyzes the images of the garment, or of the plurality of garments corresponding to the same wearer, to assess the amount of surface meeting the pre-set parameters;
   E) assessment step, in which the dedicated software processes the data regarding at least the global colorimetry of the garment, or of the plurality of garments corresponding to the same wearer, with that regarding the morphology and to the size, to give feedback on whether the garment, or the garments, meets/meet the pre-set parameters;
   F) saving in memory step, in which the dedicated software saves, in the common memory to which it is connected, in chronological order, the data of each analyzed garment, possibly associating it with other garments corresponding to the same wearer. Advantageously, said data at least regards the identification, the captured images and the assessment result carried out;
   G) sorting step, in which the garments which have been approved in assessment step are directed towards a first exit track, while the garments which have been rejected in assessment step are directed towards a second exit track.

Advantageously, in a preferred version of the present invention, the system is also provided with at least one common display, preferably touch-screen, which acts as a communication interface between the software and the operator for managing and/or controlling the system. Some functionalities offered by the display can be, by way of a non-limiting example, the display of the images that are the object of analysis, the graphic image of which surfaces are deemed suitable and which are not with respect to the analysis parameters, etc.

Advantageously, due to its characteristics, the present system allows complete operative autonomy without any operator having to be physically present during the operation thereof. One of the main characteristics that makes the use of the present system particularly advantageous, also in terms of possible future uses, lies in the possibility to modify the parameters according to which a garment is approved or rejected. This will be possible due to a simple knob arranged inside or in proximity to the tunnel or, even more advantageously, through any one adjustment system integrated in the display just described and in said software.

A more complete embodiment of the present invention, with accessories, provides for supplying an App for electronic devices downloadable by all wearers, which allows them to identify their own garment (through said identification device) and to have access to the data present in a memory regarding at least the most recent assessment obtained from the garment identified by the dedicated software.

Possibly, said App may advantageously enable the display of the chronology of the garment images captured in the various image acquisition steps conducted, of the chronology of the assessments of said identified garment and the position at every instant of such garment in the production process.

The advantages offered by the present invention are evident in light of the description set forth up to now and will be even clearer from the enclosed figures and relative detailed description.

DESCRIPTION OF THE FIGURES

The invention will be described hereinbelow in at least one preferred embodiment by way of a non-limiting example with the aid of the enclosed figures, in which:

In FIG. 1(a), a section is visible in which the tunnel 100 is seen with the movement mechanism 40 divided into entry track 41, internal track 43 and pair of exit tracks 42-42'. The garments are seen in transit, each of which provided with its identification device 30. Inside the tunnel 100, the light sources 10 are schematized together with the pair of image capturing devices 20-20' and the identification sensor 31. Outside the tunnel 100, the display 50 is seen, in proximity to which the knob 60 is arranged for adjusting the acceptability parameters. In FIG. 1(b), the tunnel 100 is shown from above, in a manner so as to make the garment movement mechanism 40 more clearly visible, with the entry track 41, the internal track 43 and the pair of exit tracks 42-42' on which the garments are sorted based on the assessment result.

DETAILED DESCRIPTION OF THE INVENTION

The present invention will now be illustrated merely by way of a non-limiting or non-constraining example, with the aid of the figures which illustrate several embodiments with regard to the present inventive concept.

Figure 1:
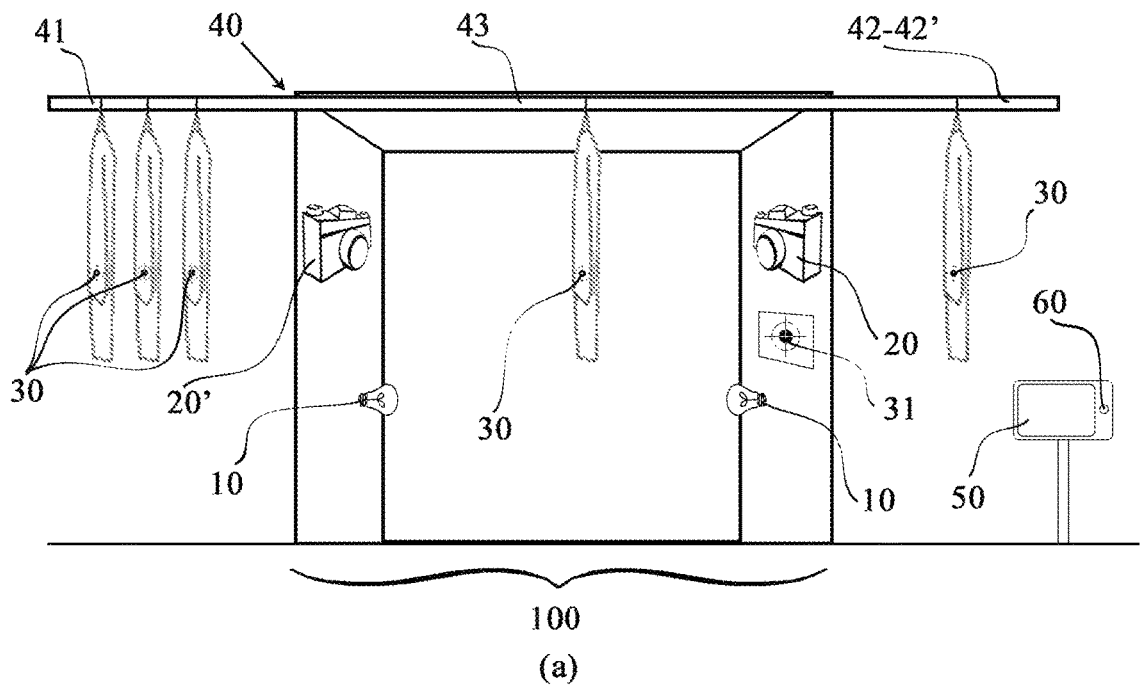
FIG. 1 shows a scheme of one of the possible embodiments of the plant according to the present invention.
Figure 1:
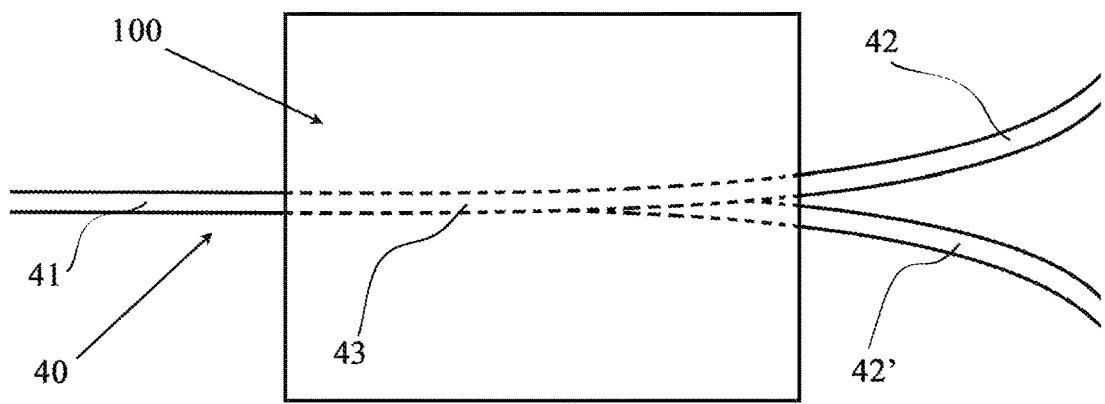

With reference to FIG. 1, one of the possible schemes is shown for attaining the garment analysis and certification plant that uses the system, object of the present invention. In particular, see a central chamber, conventionally termed tunnel 100, within which a light source 10 illuminates a garment to be analyzed, while the same is photographed by at least one pair of image capturing devices 20-20'.

The represented garment is a jacket, but the system described in detail hereinbelow is suitable to analyze and to assess any type of garment, even special garments, especially suitable for high visibility such as vests, jackets, pants, gloves, hats or any other garment suitable to instantly identify a wearer even in poor visibility conditions.

Figure 2:
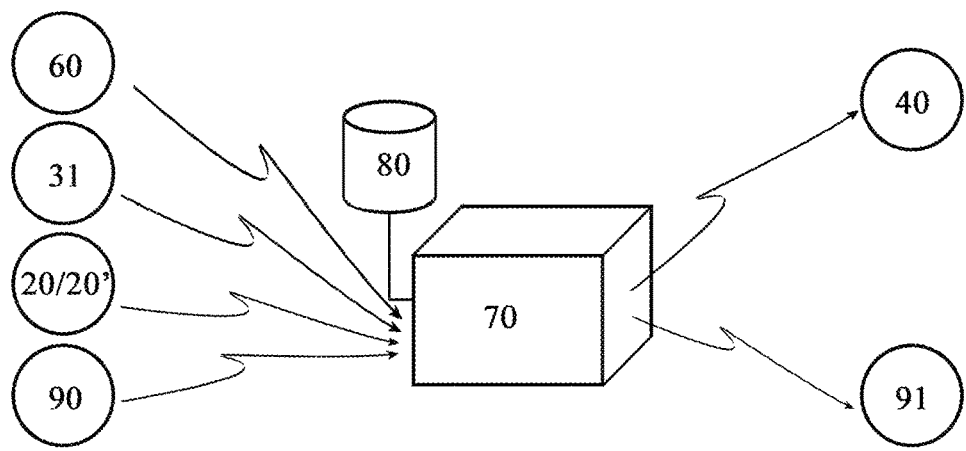
FIG. 2 illustrates an operating diagram for the dedicated software 70 connected to the relative memory 80. Said dedicated software, in one of the possible operating schemes, receives information from the identification sensor 31, from the pair of image capturing devices 20-20', from the possible temperature sensors 90 and is set by the adjusting knob 60. After the processing of the received data, said dedicated software 70 acts on the movement mechanism 40, sorting the garments between those approved and those rejected, and it acts on the possible forced ventilation system 91.
Figure 3:
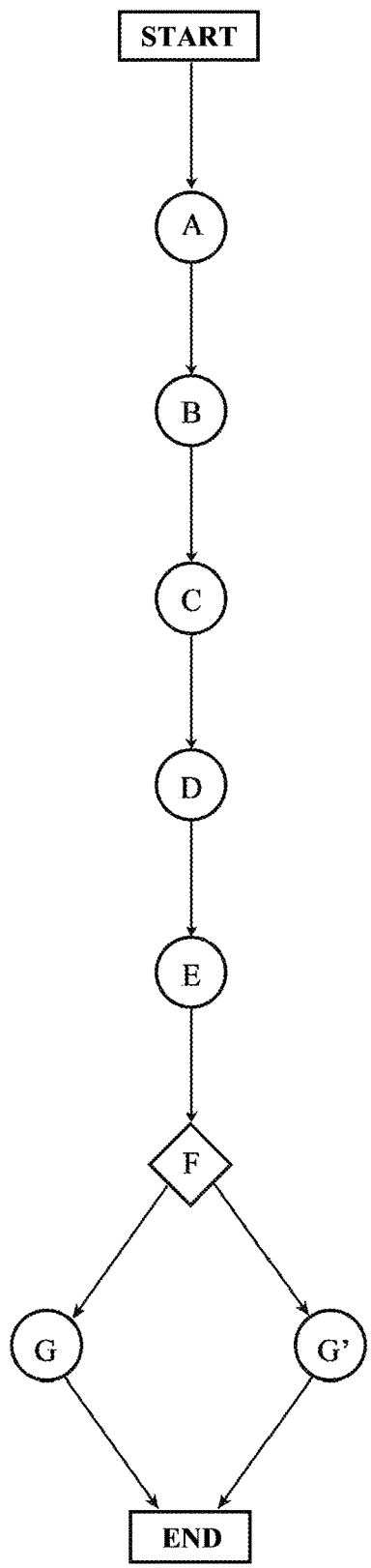
FIG. 3 shows a flow diagram for the operation of the present system. Step A indicates the identification of the garment; step B regards the entry of the garment in the tunnel 100; step C refers to the acquisition of the images of the garment; step D follows for the colorimetric, morphological and metric analysis of the image; afterwards, there is step E for the global assessment of the garment and the saving of the data in the memory (step F); based on the assessment result, the garment is directed towards the approved garments (step G) or towards the rejected garments (step G').

The garments are transported inside the tunnel 100 by a common movement system 40, preferably configured with tracks. In particular, as better represented in FIG. 2, said movement system 40 is constituted by an entry track 41, a track 43 inside the tunnel 100 and a pair of exit tracks 42-42' on which the garments deemed suitable for certification/approval are separated from those deemed unsuitable. In other words, on a first exit track 42, the garments will be directed which had a positive assessment result, while on a second exit track 42', the rejected garments will be directed.

Returning to the technical specifications of the plant according to the present invention, said tunnel 100 can be constituted by a fixed or disassemblable structure and, if the situation required it, it can be completely closed, or made as an actual darkroom in which the light of the external environment cannot in any manner filter inside.

In this particular embodiment, in order to preserve the correct operation of all the components of the system inside the tunnel 100, at least one temperature sensor 90 is adapted, upon exceeding a predetermined temperature inside the tunnel 100, to reversibly activate a common forced ventilation system 91. As an addition to this embodiment, in order to ensure the constant brightness intensity at the time of acquisition of the images and/or detection of the measurements, the internal space of said tunnel 100 is provided with at least one exposure meter and/or luxmeter, which by interfacing the detected data with said software 70, is used for monitoring the light intensity inside the tunnel 100 and adjusting it through suitable potentiometers.

The equipment inside the tunnel 100, which allows the correct performance of all the steps necessary for the assessment, includes apparatuses commonly available on the market: said light source 10 is constituted by at least one, preferably two or in any case a plurality of common lamps available on the market, such as halogen lamps, LED lamps led, UV or IR illuminators, laser lights or the like. The image capturing devices 20-20' must be positioned in a manner such that at least one front image capturing device 20 is suitable to take a photograph of the front part of the garment and at least one rear image capturing device 20' is suitable to take a photograph of the rear part of the garment. Also with reference to these devices, they are constituted by common CCD video cameras, CMOS video cameras, IR or UV sensors, laser sensors or the like.

Still inside said tunnel 100, a common automatic gripping mechanism is arranged which is suitable to grip several strips of the garment to be analyzed in order to reversibly arrange it in a spread configuration, in which substantially the entire surface of said garment to be analyzed is exposed to the light of said light source 10, and it can be photographed by said image capturing devices 20-20'. In this manner, the availability of the garment to be analyzed by the image capturing devices 20-20' and hence by the dedicated software 70 is improved, consequently improving the reliability of the assessment.

As represented in FIG. 1, each garment is provided with a corresponding identification device 30 uniquely associated therewith and adapted to be recognized by an identification sensor 31 placed at the inlet of or inside the tunnel 100. Such identification device and sensor 30, 31 are preferably constituted by common barcode readers or RFID readers.

Often, such high visibility garments are worn in a manner associated with other garments (jacket-pants outfit or in association with gloves or hat). In this case, the identification system will be suitably configured to ensure that the identification sensor 31 is able to associate the garments worn by the same wearer. In this case, their analysis and assessment could also be carried out at the same time.

The procedure of assessment of a garment or of a plurality of garments corresponding to the same wearer are:

(A) identification step; in said identification step (A), one of the garments to be analyzed or a plurality of garments to be analyzed, each of which provided with the corresponding identification device 30, is transported in proximity to the identification sensor 31 by said movement mechanism 40, in order to uniquely associate each of said garments with a wearer;

(B) entry step; in said entry step (B) said garment to be analyzed, or said plurality of garments corresponding to the same wearer, is introduced inside said tunnel 100, passing from said entry track 41 to said internal track 43. Based on the position of the identification sensor 31, the identification step (A) and the entry step (B) can be reversed;

(C) image acquisition step; in said image acquisition step (C), after said automatic gripping mechanism has arranged the garment, or the associated garments to be analyzed, in said spread configuration, said image capturing devices 20-20' take at least one pair of photographs for each garment, respectively of the front part and of the rear part of the garment to be analyzed. Said images are immediately transmitted to said software 70. At the end of the image acquisition, said automatic gripping mechanism is suitable to release the previously gripped strips of the garment or associated garments to be analyzed, returning the garment or the garments to the initial configuration;

(D) analysis step; in said analysis step (D), said common dedicated software 70 analyzes the images of the garment, or of the plurality of garments corresponding to the same wearer, to assess the amount of surface meeting the pre-set parameters;

(E) assessment step; in said assessment step (E), said common dedicated software 70 processes the data regarding at least the global colorimetry of the garment, or of the plurality of garments corresponding to the same wearer, with that regarding the morphology and size, to provide feedback on whether the garment, or the plurality of garments corresponding to the same wearer, meets the pre-set parameters;

(F) saving in memory step; in said saving in memory step (F), said common dedicated software 70 saves, in the memory 80 connected to the software 70, in chronological order, the data of each analyzed garment, possibly associating it with at least one further garment corresponding to the same wearer, said data regarding at least the identification, the captured images and the assessment result;

(G) sorting step; in said sorting step (G), the garments, or the plurality of garments corresponding to the same wearer which have been approved in assessment step (E), are directed towards a first exit track 42, while the garments, or the plurality of garments corresponding to the wearer which have been rejected in assessment step (E) are directed towards a second exit track 42'.

Still with reference to FIG. 1, on the side of the tunnel 100, a control column is visible that is provided with a display 50 and with an adjustment device 60, constituted by a knob. This is only one of the possible embodiments of the system according to the present invention. Due to the display 50, in fact, the communication between said software 70 and the operator for managing the system is simplified.

In addition, said display 50 can be suitable to enable the display of the images captured in said image acquisition step (C) and to provide a scheme of which surfaces of said garment, or of said plurality of garments corresponding to the same wearer, correspond to said pre-set parameters.

The knob or any other adjustment device 60, finally, has a fundamental role in managing the analysis. Indeed, it is adapted to adjust the colorimetry parameters according to which a garment is approved or rejected, thus making the system extremely flexible and personalizable.

An additional item that the present invention offers in its preferred embodiment, to all wearers provided with an electronic device such as a smartphone or a tablet, is the possibility to download an App.

Through this application (App), the recognition of each garment is enabled through said recognition device 30 and the access to the memory 80 regarding the identified garment is also enabled. Among the data that the wearer will be able to consult, by way of a non-limiting example, is that regarding the most recent assessment obtained from the identified garment, the chronology of the images of the garment and of the assessments thereof and the position at every instant of the wearer's garment in the production process.

Finally, it is clear that modifications, additions or variations can be made to the invention described up to now that are obvious for a man skilled in the art, without departing from the protective scope provided by the enclosed claims.

The invention claimed is:

1. A method for identifying and certifying garments, to analyze morphological, metrical and colorimetric state of a given garment according to pre-set parameters, and to provide, at an end of said analysis, an assessment on whether said given garment meets said pre-set parameters, the method comprising:

(A) using a system comprising:

an identification device (30) that attaches to the given garment to be analyzed;

a tunnel (100);

an identification sensor (31) positioned with respect to the tunnel (100) to wirelessly recognize the identification device (30) to thereby identify the given garment to be analyzed;

a movement mechanism (40) extending through the tunnel (100) and comprising a track divided into a first entry area track (41) located at an entrance to the tunnel (100), a second internal area track (43) within the tunnel (100) and a pair of exit tracks (42, 42') that extend through an exit of the tunnel (100), the movement mechanism configured to transfer the given garment on the track from the entrance of the tunnel (100), through the tunnel (100) and out the exit of the tunnel (100), the pair of exit tracks (42, 42') defined a first exit track (42) for approved garments and a second exit track (42') for rejected garments, wherein the movement mechanism (40) is configured to selectively direct the given garment from the internal track (43) to one of the first exit track (42) for approved garments and the second exit track (42') for rejected garments;

a light source (10) positioned and configured to illuminate the given garment within the tunnel (100);

at least one pair of image capturing devices (20, 20') positioned and configured to photograph the given garment being illuminated by the light source (10), said at least one pair of image capturing devices (20, 20') comprising a front image capturing device (20) configured to take a photograph of a front part of the given garment, and a rear image capturing device (20') configured to take a photograph of a rear part of the given garment;

a display (50);

an adjustment device (60) located in proximity to the display (50), the adjustment device (60) being controllable by an operator; and software (70) connected to a memory (80), the software (70) connected to a memory (80) being operatively connected to said at least one pair of image capturing devices (20, 20'), to the identification sensor (31), to the movement mechanism (40), to the adjustment device (60), the software (70) receiving information from the identification sensor (31), from said at least one pair of image capturing devices (20, 20');

(B) an identification step of using the movement mechanism (40) to arrange the given garment to be analyzed to a front part of the tunnel, so that the given garment provided with the identification device (30) is in proximity to the identification sensor (31) and having identification sensor (31) wirelessly recognize the identification device (30) to provide an identification that associates said given garment with a given wearer;

(C) an entry step of using the movement mechanism (40) to introduce said given garment to be analyzed into said tunnel (100) including passing along said first entry area track (41) to said second internal area track (43);

(D) an image acquisition step at an area of said second internal area track (43), wherein said given garment to be analyzed is changed from an initial configuration to a spread configuration and said at least one pair of image capturing devices (20, 20') take plural images, respectively, of the front part and of the rear part of the given garment to be analyzed; said at least one pair of image capturing devices (20, 20') transmitting said plural images to said software (70) for said software (70) to process the plural images; wherein at an end of said image acquisition, returning said given garment to the initial configuration;

(E) an analysis step of said software (70) analyzing the plural images of the given garment to assess an amount of surface of the given garment meeting the pre-set parameters;

(F) an assessment step of said software (70) processing data regarding at least colorimetry and overall reflectance of the given garment, including morphology and size of the given garment, to give results on whether the given garment meets the pre-set parameters, wherein the given garment is approved by software (70) when the given garment meets the pre-set parameters, and the given garment is rejected by the software (70) when the given garment does not meet the pre-set parameters;

(G) a saving in memory step of said software (70) saving in said memory (80) data regarding the given garment, said data including at least the identification that associates said given garment with the given wearer, the plural images from the image acquisition step, and the results from the assessment step; and (H) a sorting step of said movement mechanism (40) transferring the given garment to the first exit track (42) when the software has approved the given garment and transferring the given garment to the second exit track (42') when the software has rejected the given garment, wherein said pre-set parameters used in the analysis step and the assessment step are changeable by the adjustment device (60) being controlled by the operator.

2. The method according to claim 1, comprising analyzing a plurality of the given garment associated to a same wearer, by:

providing the identification device (30) on each given garment that is associated to the same wearer, and then performing each of the entry step, the image acquisition step, the analysis step, the assessment step, the saving step, and the sorting step on each given garment having been provided with the identification device (30) associated to the same wearer.

3. The method according to claim 1, wherein said identification step and said entry step are interchangeable depending on the position of said identification sensor (31) being inside or outside said tunnel (100).

4. The method according to claim 1, further comprising using a display (50) arranged as a communication interface between said software (70) and the operator; said display (50) displaying the images captured in said image acquisition step and providing a diagram showing which surfaces of said given garment satisfy said pre-set parameters.

5. The method according to claim 1, wherein said light source (10) is constituted by at least one lamp.

6. The method according to claim 1, wherein said at least one pair of image capturing devices (20, 20') are constituted by cameras.

7. The method according to claim 1, wherein said identification devices (30) and said identification sensor (31) are barcode readers or RFID readers.

8. The method according to claim 1, wherein said tunnel (100) is constituted by a structure completely closed by opaque walls that prevent any contamination of interior artificial light by light from outside said tunnel (100).

9. The method according to claim 8, wherein said tunnel (100) is internally provided with at least one temperature sensor (90) to communicate data regarding interior temperature of said tunnel (100) to said software (70); the software (70) reversibly activating a forced ventilation system (91) when the temperature detected by said at least one temperature sensor (90) exceeds a predetermined threshold value.

10. The method according to claim 1, wherein said tunnel (100) is provided with an exposure meter and/or a luxmeter to detect data regarding interior brightness of said tunnel (100) and to send said data regarding the interior brightness of said tunnel (100) to said software (70); said software (70) reversibly and automatically adjusting the brightness of said light source (10), through at least one adjustment potentiometer connected to said light source (10), to maintain the interior brightness of said tunnel (100) within pre-established parameters.

11. The method according to claim 1, wherein said tunnel (100) has a fixed or reversibly disassemblable structure.

12. The method according to claim 1, further comprising using an application downloaded to an electronic device to recognize each garment, through said identification device (30), and to provide at least data regarding a most recent assessment obtained from the given garment identified by said software (70).

13. The method according to claim 12, using said application to access chronology, present in said memory (80) of said software (70), of the acquired images and assessments carried out over a lifetime of the given garment and a position of the given garment during a production process.

14. The method according to claim 1, wherein the given garment is one of the group consisting of jackets, vests, pants, gloves, and hats.

15. The method of claim 1, wherein the at least one identification sensor (31) is arranged inside said tunnel (100).

16. The method of claim 15, wherein the adjustment device (60) is located in said tunnel (100).

17. The method according to claim 2, wherein said identification step and said entry step are interchangeable depending on the position of said identification sensor (31) being inside or outside said tunnel (100).

18. The method of claim 4, wherein the display (50) is a touch screen device, and wherein said adjustment device (60) for adjusting said parameters is operated through said display (50).

19. The method of claim 1, wherein said light source (10) comprises a plurality of the lamps.

20. The method of claim 9, wherein the at least one temperature sensor (90) comprises plural temperature sensors.

* * * * *